United States Patent [19]
Khan et al.

[11] Patent Number: 6,046,143
[45] Date of Patent: *Apr. 4, 2000

[54] WATER SOLUBLE LUBRICANT FOR MEDICAL DEVICES

[75] Inventors: Azhar J. Khan, West Valley City; Mohammad A. Khan, Sandy, both of Utah

[73] Assignee: Becton Dickinson and Company, Franklin Lakes, N.J.

[*] Notice: This patent is subject to a terminal disclaimer.

[21] Appl. No.: 09/040,758

[22] Filed: Mar. 18, 1998

Related U.S. Application Data

[63] Continuation-in-part of application No. 08/798,810, Feb. 12, 1997, which is a continuation of application No. 08/670,296, Jun. 27, 1996, Pat. No. 5,653,695, which is a continuation of application No. 08/294,212, Aug. 22, 1994, abandoned.

[51] Int. Cl.$^7$ ......................... C10M 155/02; A61M 25/00
[52] U.S. Cl. ......................... 508/208; 508/204; 604/265; 514/63
[58] Field of Search ............................................. 508/208

[56] References Cited

U.S. PATENT DOCUMENTS

| | | | |
|---|---|---|---|
| 3,574,673 | 4/1971 | Schweiger et al. | 30/32 |
| 3,756,052 | 9/1973 | Quaal et al. | 508/208 |
| 3,912,665 | 10/1975 | Spitzer | 260/2.5 E |

(List continued on next page.)

FOREIGN PATENT DOCUMENTS 0 627 474 A1  12/1994  European Pat. Off. .

OTHER PUBLICATIONS

Union Carbide Chemicals and Plastic Company, Inc., Material Safety Data Sheet for Y–12686, Effective Date Jun. 1, 1992, Danbury, CT.
Union Carbide Chemicals and Plastic Company, Inc., Material Safety Data Sheet for Y–12613, Effective Date Sep. 17, 1992, Danbury, CT.
Hoffman–LaRoche, Inc., Material Safety Data Sheet for d, 1–alpha–Tocopheral, Effective Jul. 20, 1992, Nutley, NJ.
W. Nikolowski, Vitamin E in Dermatology, Vitamins, pp. 1–6, 1973 (no month).
ICI Americas Inc., Cosmocil CQ Brochure (date N/A).
ICI Americas Inc., Baquacil Brochure (date N/A).
Union Carbide Chemicals and Plastics Company, Inc., Silwet Surfactants Brochure (date N/A).
The United States Pharmacopeia, pp. 1451–1453, 1990, Rockville, MD (no month).
PPG Industries, Inc., Masil Silicone Surfactants Technical/Quality Bulletin (date N/A).

*Primary Examiner*—Ellen M. McAvoy
*Attorney, Agent, or Firm*—Eric M. Lee; Scott S. Servilla

[57] ABSTRACT

This invention relates to a new water soluble lubricant for a medical device, such as a catheter and an introducer needle. The lubricant is a silicone based water soluble compound. Preferably, a silicone surfactant is used such as a block copolymer polyalkylene oxide-modified polydimethylsiloxane. Alternatively, an alkylene oxide modified silicone glycol may be used as the lubricant. In addition, lecithin can be added as a lubricant. The lubrication solution includes a solution stabilizer to clarify the solution and antimicrobial agents to inhibit microbial growth in the water solution or on the coated product. Vitamin E or its derivatives may also be used in the lubrication solution.

16 Claims, 1 Drawing Sheet

U.S. PATENT DOCUMENTS

| | | | |
|---|---|---|---|
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,720,521 | 1/1988 | Spielvogel et al. | 524/862 |
| 4,758,595 | 7/1988 | Ogunbiyi et al. | 424/78.26 |
| 4,814,231 | 3/1989 | Onohara | 428/425.5 |
| 4,836,986 | 6/1989 | Ogunbiyi et al. | 422/28 |
| 4,837,047 | 6/1989 | Sato | 422/41 |
| 4,838,876 | 6/1989 | Wong et al. | 604/265 |
| 4,842,889 | 6/1989 | Hu et al. | 427/38 |
| 4,844,986 | 7/1989 | Karakelle et al. | 428/447 |
| 4,904,433 | 2/1990 | Williamitis | 264/130 |
| 4,973,643 | 11/1990 | O'Lenick, Jr. | 528/15 |
| 5,013,717 | 5/1991 | Solomon et al. | 514/56 |
| 5,026,607 | 6/1991 | Kiezulas | 428/423 |
| 5,037,419 | 8/1991 | Valentine | 604/408 |
| 5,043,161 | 8/1991 | Scarpelli | 424/401 |
| 5,047,159 | 9/1991 | Zehler | 252/49 |
| 5,061,738 | 10/1991 | Solomon et al. | 523/100 |
| 5,071,706 | 12/1991 | Soper | 428/402.2 |
| 5,185,006 | 2/1993 | Williamitis et al. | 604/265 |
| 5,266,359 | 11/1993 | Spielvogel | 427/388.4 |
| 5,272,012 | 12/1993 | Opolski | 428/423.1 |
| 5,336,209 | 8/1994 | Porzilli | 604/307 |
| 5,338,312 | 8/1994 | Montgomery | 604/230 |
| 5,344,411 | 9/1994 | Domb et al. | 604/265 |
| 5,383,903 | 1/1995 | Totakura | 606/228 |
| 5,409,463 | 4/1995 | Thomas et al. | 604/167 |
| 5,431,832 | 7/1995 | Crowe et al. | 508/208 |
| 5,653,695 | 8/1997 | Hopkins et al. | 508/208 |
| 5,688,747 | 11/1997 | Khan et al. | 508/208 |

WATER SOLUBLE LUBRICANT FOR MEDICAL DEVICES

This application is a continuation-in-part of application Ser. No. 08/798,810 filed Feb. 12, 1997, pending, which is a continuation of application Ser. No. 08/670,296 filed Jun. 27, 1996, now U.S. Pat. No. 5,653,695; which is a continuation of application Ser. No. 08/294,212 filed Aug. 22, 1994, now abandoned.

BACKGROUND OF THE INVENTION

This invention relates in general to a novel lubricant used in connection with medical devices such as intravenous (IV) catheters.

IV catheters are designed to infuse normal IV solutions, including antibiotics and other drugs, into a patient. The typical catheter is hollow and is extruded out of a suitable plastic material such as Teflon, polyvinyl chloride, polyethylene, polyurethane or polyether urethane. These catheters are also used to withdraw blood from the patient for normal blood-gas analysis as well as other blood work. In order to insert an IV catheter into a patient, an introducer needle is used. The needle is typically stainless steel and is hollow. Its distal tip is ground to a sharp tip for easy insertion into the patient. The catheter is also hollow and is initially located coaxially around the introducer needle in an "over the needle" arrangement. The internal diameter of the catheter tip is slightly less than the outer diameter of the tip of the needle so that the catheter tip has an interference fit on the needle tip. The interference fit is necessary so that when the catheter and introducer needle assembly is taken out of the package, the catheter remains snugly on the needle and does not easily slip off. This interference fit also facilitates insertion of the catheter and introducer needle assembly into the patient's vein because it minimizes the chance that the catheter tip will fold over or peel back on the needle tip.

Placement of the catheter and introducer needle into the patient may cause sharp pain to the patient. In order to facilitate insertion of the catheter and introducer needle into the vein and to minimize patient discomfort, the catheter and introducer needle can both be lubricated. Most IV catheters are lubricated with polydimethylsiloxane silicone fluid. However, some IV catheters are not lubricated at all.

The polydimethylsiloxane silicone fluid may be applied to the surface of the catheter and needle by wiping the surfaces with the lubricant. Alternatively, the catheter and needle can be separately dipped into a solution of polydimethylsiloxane silicone fluid and a solvent. This is generally the preferred method of applying the lubricant because a consistent, controlled and uniform coating can be achieved. The polydimethylsiloxane silicone fluid must be dissolved in an organic solvent because the silicone oil in this compound is hydrophobic. Typically, the solution contains 2.5% silicone oil. The catheter and needle are then separately dipped into this solution.

Until recently the preferred solvent has been freon because it is non-flammable and flashes off, i.e. evaporates, readily after the polydimethylsiloxane silicone fluid solution has been applied to the catheter and needle. Although freon has been preferred, it does suffer some drawbacks. For instance, the high evaporation rate of freon causes the polydimethylsiloxane silicone fluid to concentrate on the surface of the solution in which the catheter and needle are dipped. Because of this high evaporation rate, the solution is difficult to control. Moreover this solution is expensive because of the large loss of freon during the coating process.

In addition, freon is a chlorofluorocarbon (CFC) which is thought to react with and destroy the earth's protective ozone layer. Thus the manufacture and use of such CFC's will eventually cease in the near future.

Other solvents will have to be used in order for silicone fluid to be applied to catheters and introducer needles as a lubricant. Other solvents include alcohol and hydrocarbons. However, alcohol and hydrocarbons are highly combustible and are therefore too dangerous for use in manufacturing.

Previous efforts have been made to provide a lubrication system that uses water as the solvent. Such systems typically are a three part system that uses a lubricant, a surfactant and water. U.S. Pat. No. 5,266,359 discloses such a three part system that uses water as the solvent. Although, such three part lubrication systems that use water as the solvent are "environmentally friendly" and are not flammable, they could be improved. Since a three part lubrication system by definition requires three separate elements, a certain amount of cost is associated with the materials and manufacturing processing needed to apply the system to a medical device to be lubricated.

Another important issue concerning IV catheters is the shape of the catheter tip. The shape of the catheter tip must produce minimal trauma to the patient during insertion of the catheter into the patient and while the catheter is in place in the patient. Such a preferred tip shape that provides these characteristics has a tapered outer wall and an angled tip and is disclosed in U.S. Pat. No. 4,588,398. A process for making that catheter tip is disclosed in U.S. Pat. No. 4,661,300. In this process, the catheter is placed on a mandrel. A die having an interior molding surface, which is tapered according to the tip desired on the catheter, is aligned axially with the mandrel. The catheter tip is heated, typically using RF energy, so that it is flowable. The mandrel and die are brought together so the distal edge of the mandrel engages the tapered portion of the die. This action cleanly forms a smooth and uniform tapered tip for the catheter.

After the catheter is tipped, it must be free of defects such as incomplete formation, substantial flash or jagged edges. The tip must also look smooth and be free of roll-overs. In addition, the length of the catheter must remain within a desired specification after the tipping process. If, during the tipping process, the thermoplastic material sticks to the die or the mandrel, the length will vary greatly due to stretching and the tip will not be free of defects. Visual or microscopic examination may be used to determine if there are any tip defects and if the length of the catheter is within specifications.

Typically a lubricant is used to allow the tipped catheter to be easily removed from the mandrel and die. If a lubricant is not used, the tipped catheter could stick to the mandrel or die resulting in a deformed catheter when it is removed from the mandrel or die. Standard tipping lubricants include polydimethyl siloxanes such as Dow Corning DC 360 or curable silicones such as Dow Corning 44159 MDX which are amine terminated and moisture curable. Non-curable amine terminated polydimethyl siloxanes have also been used for this purpose. Such lubricants are described in, for example, U.S. Pat. Nos. 3,574,673; 4,904,433; and 5,185,006. Again, these silicone oils used are problematic as discussed above.

SUMMARY OF THE INVENTION

It is therefore an object of this invention to provide a lubrication solution for a medical device, such as a catheter and an introducer needle assembly, that is inexpensive and easy to control.

It is another object of this invention to provide a lubricant for a medical device, such as a catheter and an introducer needle assembly, that does not require the use of a CFC as a solvent.

It is yet another object of this invention to provide a lubrication solution for a medical device, such as a catheter and an introducer needle assembly, that is "environmentally friendly."

It is still another object of this invention to provide a lubrication solution for a medical device, such as a catheter and an introducer needle assembly, that is not flammable.

It is a further object of this invention to provide a lubrication solution that requires less material and cost than other lubrication solutions.

The lubrication solution of this invention is a two part system that uses water as the solvent. The lubricant is a silicone based water soluble material. No other material is needed for lubricity. Instead the silicone in the material alone provides the lubricity and the material is soluble in water. Thus, the solution of the silicone based water soluble material and water allows the silicone to be easily applied to the medical device or other apparatus and, when the water evaporates, ensures that the surface on which the material is applied is lubricious. Preferably, the silicone based water soluble material is a silicone surfactant or a silicone glycol. The silicone material is preferably non-ionic because it may have lower toxicity than the ionic form. The lubrication solution may also include vitamin E or its derivatives. In addition, the lubrication solution in which the device to be lubricated is dipped may include a solution stabilizer to clarify the solution and antimicrobial agents to inhibit microbial growth in the water solution or on the coated product.

The tipping process of this invention requires that the tip portion of the catheter blank be dipped in the solution or to otherwise have this solution applied to the surfaces to be lubricated such as by brushing or spraying the solution onto such surfaces. Once the water evaporates, the catheter blank is mounted on a mandrel and heated. A die and the mandrel are brought into engagement to form the catheter tip. The tipped catheter is then easily and quickly removed from the die and the mandrel.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
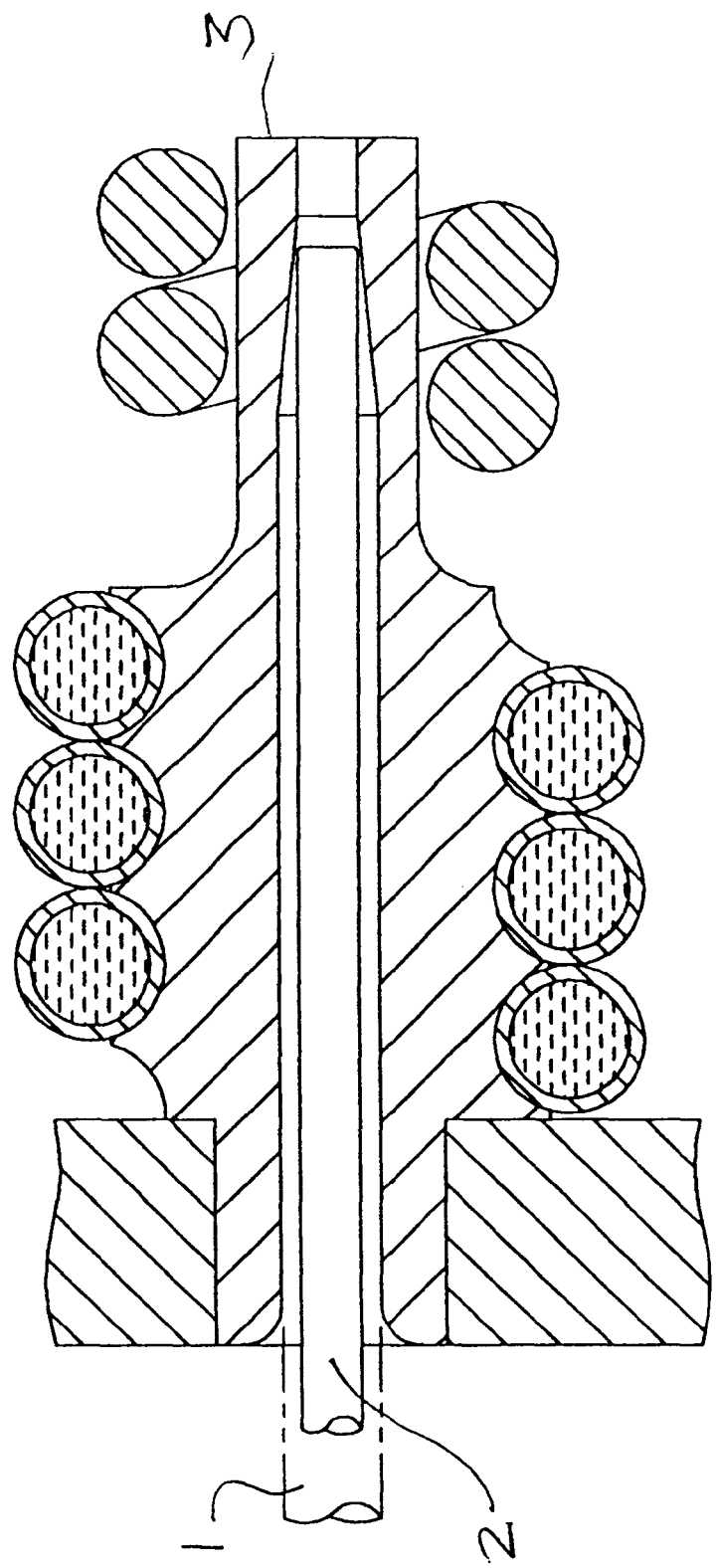
FIG. 1 is a cross-sectional view of a portion of a die and mandrel arrangement with a catheter blank thereon with the mandrel engaged with the die to form the catheter tip.

Although this invention is discussed in terms of its application to IV catheters and introducer needles, it is to be understood that this invention could be used on other medical devices where a lubricious surface on the device is desirable.

This invention uses a silicone based water soluble compound as the lubricant since the silicone in the compound is a good lubricating fluid. The silicone based water soluble compound should comprise between about 0.25% to about 40.0%, preferably from about 2.0% to about 6.0% of the lubrication solution. The lubrication solution may also include vitamin E or its derivatives. Preferably between about 0.1% to about 1.0% of vitamin E or its derivative is used. The lubrication solution should also include a solution stabilizer to clarify the solution and antimicrobial agents to inhibit microbial growth in the water solution or on the coated product. The solution stabilizer should comprise between about 0.1% to about 10%, preferably between about 0.2% to about 1.0% of the solution. The antimicrobial agent should comprise between about 0.001% to about 5.0%, preferably between about 0.002% to about 0.05% of the solution.

The lubrication solution of this invention is a two part system of the silicone based water soluble compound and water. One silicone based water soluble compound that can be used is a silicone surfactant such as a Silwet silicone surfactant. Silwet is the trade name of a class of silicone surfactants sold by OSI Specialities, Inc. These surfactants are polyalkylene oxide-modified polydimethylsiloxane block copolymers. They are similar to standard silicone fluids except the polydimethylsiloxane backbone has polyalkylene oxide side chains similar to non-ionic surfactants like poly-(oxyethylene) poly-(oxypropylene) block copolymers known as pluronic polyols. The side chains are terminated with either hydroxy or low alkoxy end groups. One of these surfactants, Silwet L7001 has a molecular weight of 20,000 and a viscosity of 1700 centistokes. Its chemical formula is shown below:

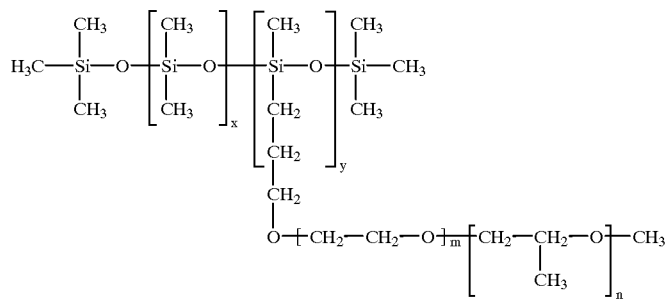

The amino-modified silicone polyether copolymer can also be used as the lubricant alone or in combination with the polyalkylene oxide-modified polydimethyl-siloxane block copolymer. These surfactants are soluble in a wide variety of solvents such as CFC, alcohol, acetone, and water. The polyalkylene oxide chains also promote wetting on polyether urethane surfaces. Polyether urethane is a material that is used for making IV catheters. The similarity in chemical structure between these side chains and the soft segment of polyether urethane promote the surfactant's affinity for the catheter surface.

Although surfactants can be irritating or toxic depending on exposure levels, the Silwet silicone surfactants are copolymers of two polymeric materials, silicone fluids and polyalkylene oxides, which are low in toxicity. In particular, Silwet L7001 has a very low order of acute toxicity by swallowing, or skin penetration and is minimally irritating to the skin and is not irritating to the eyes. Thus, there should be no toxicity problems when the lubricant of this invention is used on a patient.

Another silicone based water soluble compound that can be used as the lubricant of this invention is an alkylene oxide modified silicone glycol. A preferred compound is sold under the trade name Masil which is a class of alkylene oxide modified silicone glycols sold by PPG. These compounds have the following structural formula:

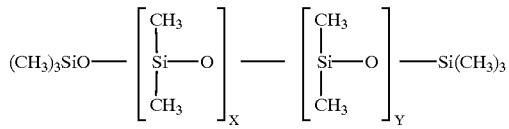

where R is defined as:

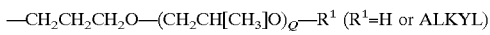

MASIL® 1066D Silicone Surfactant is similar to the model above, but the silicone-organic linkage is through an Si—O—C bond, susceptible to hydrolysis under acidic or mildly basic conditions. The alkylene oxide modified silicone glycol can be used alone as the lubricant or it can be used in combination with the silicone surfactant.

Vitamin E and its derivative, Vitamin E acetate, may also be added to the solution. Vitamin E, which is chemically known as alpha-tocopherol, is an antioxidant and thus prevents degradation of the solution. Vitamin E and its derivative, vitamin E acetate, are both oily products and also enhance the lubricity of this lubrication system. The molecular structure of vitamin E is given below:

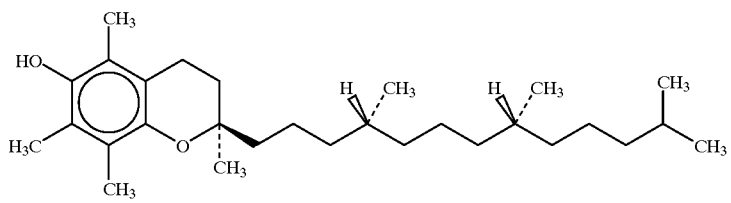

Since the lubricant solution is prepared in water, it is highly desirable that a small amount of an effective antimicrobial agent be present to serve as a preservative. In the absence of such an agent, micro-organisms may grow in the solution and make the solution toxic. There are several commercial antimicrobial agents available. These are iodophors; phenols; phenolic compounds such as para-chloro-meta-xylenol; biguanides such as chlorhexidine gluconate and polyhexamethylene biguanide hydrochloride (cosmocil). Cosmocil is used because it is less toxic than the other antimicrobial agents and is used as a preservative in contact lens cleaning solutions. The molecular structure of cosmocil is given below:

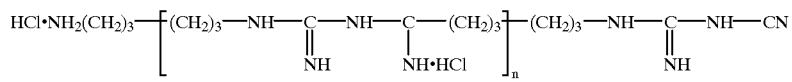

The molecular weight of this product is 2100±300.

The process of forming the catheter tip will now be described. First, the lubricant solution is applied to the surface to be lubricated, i.e. the catheter blank. The catheter blank 1 to be tipped is then mounted onto a mandrel 2 supported on a carriage (not shown). A die 3 having an interior molding surface, with at least one portion of which is tapered according to the tip desired on the finished catheter, is aligned axially with the mandrel 2. The carriage is moved toward the die 3 such that the end of the catheter blank 1 to be tipped engages the interior molding surface. The carriage is halted at a point after the catheter blank 1 has engaged the tapered portions of the interior molding surface of the die 3, and is biased toward the die 3 with only sufficient force to cause the catheter blank 1 to move further into the die as the catheter blank 1 is heated by RF energy to its melting point and begins to flow. See FIG. 1. The catheter blank 1 is then allowed to heat in the die 3 and is moved into the die 3 as it begins to melt and flow under the biasing force. The mandrel 2 is positioned so that its distal corner is against the tapered portion of the die 3, thus cleanly forming the leading edge of the catheter. The die 3 and catheter therein are then cooled, and the carriage is reversed such that the catheter may be withdrawn from the die 3. Finally, the catheter is removed from the mandrel 2. There is no flash left on the leading edge because of the contact between mandrel 2 and die 3.

The following examples show the beneficial result of using the lubricant of this invention:

EXAMPLE NO. 1

Initial studies were conducted by separately dipping 20 gauge (ga) catheters and introducer needles into 4%, 8% and 32% Silwet L7001 silicone surfactant and water solutions and then assembling the catheters and needles. The assemblies were penetration tested through 13.5 mil. thick natural latex film.

|                      | 4% Silwet L7001 | 8% Silwet L7001 | 32% Silwet L7001 |
| --- | --- | --- | --- |
| Needle tip (g)       | 24.5 (0.9) | 23.3 (2.9) | 24.3 (5.8) |
| Needle transition (g)| 18.5 (2.7) | 17.0 (2.2) | 15.0 (1.0) |
| Needle heel (g)      | 11.0 (0.7) | 10.5 (1.5) | 8.0 (0.0) |
| Catheter tip (g)     | 26.0 (3.7) | 28.3 (5.3) | 25.3 (1.9) |
| Catheter taper (g)   | 15.3 (0.8) | 15.0 (3.0) | 10.3 (0.8) |
| Catheter drag (g)    | 7.3 (1.9)  | 4.5 (0.5)  | 4.0 (0.0) |

NOTE:
() = standard deviation. Sample size = 4.

The values given represent the resistance in grams when the device is penetrated through the latex membrane. These values are comparable to those of currently marketed products that are lubricated with dimethylsiloxane fluids and are better than products that are unlubricated. This example thus shows that a silicone surfactant works as a lubricant for a catheter and/or introducer needle.

EXAMPLE NO. 2

20 gauge catheters and needles were separately dipped in a solution containing 8% Silwet L7001 silicone surfactant, 0.25% vitamin E, 0.5% vitamin E acetate, and 0.026% cosmocil. The catheters and needles were then assembled and these assemblies were penetration tested through 13.5 mil. thick natural latex film. The results are shown below:

| | |
| --- | --- |
| Needle tip (g)        | 18.3 (1.9) |
| Needle transition (g) | 14.7 (0.6) |
| Needle heel (g)       | 7.0 (0.3) |
| Catheter tip (g)      | 20.2 (2.3) |
| Catheter taper (g)    | 10.5 (0.6) |
| Catheter drag (g)     | 3.5 (1.3) |

NOTE:
() = standard deviation. Sample size = 5.

It can be seen that the use of vitamin E and/or its derivatives as part of the lubricant in the solution improves the penetration forces.

When vitamin E and/or its derivatives are included in the silicone surfactant solution, a rather cloudy solution is obtained indicating that the solution is not homogenous. If a quaternary ammonium salt is added at a certain concentration, a clear solution is obtained. For example, Sylguard, sold by Dow Corning, which is a reactive quat and benzalkonium chloride can be added to the solution. Other quaternary ammonium salts, such as benzethonium chloride, could also be used.

EXAMPLE NO. 3

A solution containing 6.0% Silwet L7001 silicone surfactant, 0.36%/o vitamin E and 1.0% benzalkonium chloride was used as the lubricant solution. In this example, the 1.0% benzalkonium chloride was in the form of 2.0% Hyamine 3500. Hyamine 3500 is a trade name for the benzalkonium chloride solution sold by Rohm and Hass and contains 50% of the active ingredient. As a comparison, a lubricant solution with no benzalkonium chloride was also used. 18 gauge catheters and needles were separately dipped and then assembled. These catheter assemblies were penetrated through dental dam (natural latex film).

|                      | No Quaternary Ammonium Salt | 1% Benzalkonium Chloride |
| --- | --- | --- |
| Needle tip (g)       | 24.3 (4.6) | 24.0 (3.6) |
| Needle transition (g)| 19.0 (1.0) | 19.3 (1.4) |
| Needle heel (g)      | 11.3 (1.2) | 10.0 (0.5) |
| Catheter tip (g)     | 19.8 (2.1) | 24.2 (2.3) |
| Catheter taper (g)   | 15.5 (0.9) | 17.3 (1.8) |
| Catheter drag (g)    | 4.8 (0.5)  | 4.9 (0.4) |

NOTE:
() = standard deviation.

These results indicate that there is no adverse effect on the lubricant caused by using a quaternary ammonium salt in the lubrication system.

EXAMPLE NO. 4

Since amino-modified silicones are lubricious when applied to metal surfaces, the following lubricant solutions were prepared.

|                                     | Lubricant I | Lubricant II |
| --- | --- | --- |
| Silicone Surfactant                 | 4.50 | 4.50 |
| Amino-modified silicone polyether copolymer | 0.00 | 0.50 |
| Vitamin E (%)                       | 0.25 | 0.25 |
| Cosmocil (PPM)                      | 50   | 50   |
| Water Q.S. to                       | 100  | 100  |

20 gauge catheter products were assembled after dipping the catheter and the introducer needle separately into the above solutions. The tip adhesion force between the catheter and the needle was measured after aging the assemblies at 90° C. for 2½ days. The results are tabulated below:

| | Tip Adhesion (lbs) |
| --- | --- |
| Lubricant I  | 0.348 (0.11) |
| Lubricant II | 0.188 (0.03) |

NOTE:
() = standard deviation.

These test results indicate that the use of an amino-modified silicone-polyether copolymer does lubricate the metal surface better than the unmodified silicone surfactant alone.

EXAMPLE NO. 5

The following statistical experiment was run to optimize the formulation of the lubrication system of this invention. The following table lists some of the composition variations used.

|                                     | Composition A | Composition B | Composition C |
| --- | --- | --- | --- |
| Silicone Surfactant                 | 3.0   | 4.5   | 6.0   |
| Amino-modified silicone polyether copolymer | 0.5   | 0.25  | 0.5   |
| Vitamin E (%)                       | 0.125 | 0.13  | 0.125 |

-continued

|  | Composition A | Composition B | Composition C |
|---|---|---|---|
| Cosmocil (PPM) | 50 | 50 | 50 |
| Water Q.S. to | 100 | 100 | 100 |

20 gauge catheter assemblies were assembled after dipping the catheters and the introducer needle separately. After aging the assemblies at 90° C. for 2½ days, these assemblies were penetration tested through thick natural latex film of 86.7 mils thickness. The thick latex was used because it is closer to the thickness of mammalian skin and because small differences in penetration forces are magnified. The results are tabulated below:

|  | Composition A | Composition B | Composition C |
|---|---|---|---|
| Needle tip (g) | 156.0 (11.7) | 150.4 (13.1) | 155.9 (9.5) |
| Catheter tip (g) | 90.6 (10.3) | 87.0 (10.5) | 98.3 (7.0) |
| Catheter drag (g) | 31.6 (2.9) | 32.0 (2.3) | 27.6 (1.8) |

NOTE:
() = standard deviation. Sample size = 8.

The above assemblies were also aged at 90° C. for two weeks to simulate a five year shelf-life and penetration tested through fresh cow skin. The results are tabulated below:

|  | Composition A | Composition B | Composition C |
|---|---|---|---|
| Needle tip (g) | 237.0 (63.7) | 226.0 (68.6) | 209.0 (46.1) |
| Catheter tip (g) | 299.0 (53.5) | 379.0 (42.7) | 378.0 (41.2) |
| Catheter taper (g) | 320.0 (37.9) | 284.0 (34.0) | 327.9 (39.4) |
| Catheter drag (g) | 51.0 (8.0) | 46.0 (9.7) | 42.0 (11.2) |

NOTE:
() = standard deviation. Sample size = 5.

These results on thick latex membrane show that the amount of silicone surfactant applied to the catheter and the needle has opposite effects on catheter drag and needle tip penetration. The higher the silicone surfactant concentration, the lower the drag, but at high lubricant concentrations the needle tip penetration value increases. On fresh cow skin, the needle tip penetration values decreased with increased concentration.

EXAMPLE NO. 6
The following formulations were tested.

| Catheter Lubricant |  | Needle Lubricant |  |
|---|---|---|---|
| Silicone Surfactant | 4.75% ± 0.25% | Silicone Surfactant | 2.38% ± 0.25% |
| Amino-modified silicone polyether copolymer | 0.525% ± 0.025% | Amino-modified silicone polyether copolymer | 0.525% ± 0.025% |
| Vitamin E | 0.263% ± 0.013% | Vitamin E | 0.263% ± 0.013% |
| Cosmocil | 50 ppm | Cosmocil | 50 ppm |
| Water .0.S. to | 100 | Water Q.S. to | 100 |

20 gauge catheters and needles were assembled as before and penetration tested through natural latex film of 13.5 mils thickness. At the same time, commercial 20 gauge Insyte® catheter products were tested under the same conditions for comparison. The results are tabulated below:

|  | Experimental Sample | Commercial Sample |
|---|---|---|
| Needle tip (g) | 22.6 (8.6) | 19.5 (5.7) |
| Needle transition (g) | 17.3 (1.9) | 13.4 (1.2) |
| Needle heel (g) | 10.9 (1.1) | 7.0 (0.6) |
| Catheter tip (g) | 18.1 (3.0) | 16.3 (2.4) |
| Catheter taper (g) | 16.2 (2.1) | 10.6 (1.0) |
| Catheter drag (g) | 4.8 (1.9) | 3.0 (0.6) |

NOTE:
() = standard deviation. Sample size 10.

As evident, the results are comparable for the commercial product and the experimental sample. The commercial sample used polydimethylsiloxane silicone fluid as the lubricant.

EXAMPLE NO. 7

22 gauge catheters and needles were assembled as before using the formulations described in Example 6 and penetration tested through sheep skin on the hind legs just below the knee. The penetration forces were measured using sensitive force transducers. The data were collected on a computer for analysis. For comparison, commercial 22 gauge catheter and needle assemblies using polydimethylsiloxane silicone fluid as the lubricant were used. The results are summarized below:

|  | Experimental Sample | Commercial Sample |
|---|---|---|
| Max. Catheter/Needle Tip (g) | 142.57 | 164.67 |
| Max. Catheter drag (g) | 70.31 | 271.68 |

As is evident, the new lubrication system is superior to the commercial product.

EXAMPLE NO. 8

Polyurethane tubes were lubricated using the formulations of this invention described in Example No. 6 as well as polydimethylsiloxane silicone fluid. These tubes were implanted into the aorta of rabbits to determine the level of associated clotting and emboli formulations. After three days the animals were sacrificed and the tubes were examined while they were still in the aorta. Clotting, if present, was photographed and recorded as to size, number and location. The kidneys were also examined for renal infarcts which would indicate that emboli had formed and traveled downstream to lodge in the small arteries of the kidney. The clotting resulting from the water based lubricant systems of the invention was less than the clotting resulting from the commercial lubricant. The calculated risk of clotting was three times less for the water based lubricant versus the commercial lubricant.

EXAMPLE NO. 9

Studies were conducted by dipping 18 gauge catheters and introducer needle assemblies into the various lubrication solutions shown below. The amounts of each ingredient is in percent by weight unless otherwise specified.

| Ingredients | 1 | 2 | 3 | 4 | 5 | 6 | 7 | 8 |
|---|---|---|---|---|---|---|---|---|
| Alkylene oxide modified silicone glycol (Masil 1066D) | 4.5 | — | — | — | 5.0 | — | — | — |
| Alkylene oxide modified silicone glycol (Masil 1066C) | — | 4.5 | — | — | — | 5.0 | — | — |
| Alkylene oxide modified silicone glycol (Masil 29) | — | — | 4.5 | — | — | — | 5.0 | — |
| Alkylene oxide modified silicone glycol (Masil 280) | — | — | — | 4.5 | — | — | — | 5.0 |
| Amino modified silicone surfactant (Y12686) | 0.5 | 0.5 | 0.5 | 0.5 | — | — | — | — |
| Vitamin E | 0.25 | 0.25 | 0.25 | 0.25 | 0.25 | 0.25 | 0.25 | 0.25 |
| Cosmocil | 50 ppm | 50 ppm | 50 ppm | 50 ppm | 50 ppm | 50 ppm | 50 ppm | 50 ppm |
| Water | 94.75 | 94.75 | 94.75 | 94.75 | 94.75 | 94.75 | 94.75 | 94.75 |

The assemblies were penetration tested through a latex film. The results are tabulated below:

| | Comp. 1 | Comp. 2 | Comp. 3 | Comp. 4 | Comp. 5[1] | Comp. 6 | Comp. 7 | Comp. 8 |
|---|---|---|---|---|---|---|---|---|
| Needle tip (g) | 21.95(3.2) | 22.80(4.3) | 20.45(1.8) | 20.65(3.1) | — | 22.95(4.2) | 20.78(4.0) | 22.70(2.5) |
| Catheter tip (g) | 13.95(1.5) | 12.65(0.7) | 12.70(0.7) | 13.85(1.0) | — | 13.10(0.9) | 14.15(1.1) | 15.40(1.1) |
| Catheter drag (g) | 3.30(0.4) | 3.86(1.5) | 3.90(1.2) | 5.15(1.0) | — | 4.15(1.0) | 5.95(1.0) | 7.44(1.2) |

NOTE: () = standard deviation. Sample size = 10.
Compound 5 was not tested because of difficulties in mixing the solution.

These results are comparable to the results tabulated in Example No. 1.

The tip adhesion force between the catheter and the needle was measured for certain solutions and tabulated below.

| Tip Adhesion | Comp. 3 | Comp. 4 | Comp. 6 |
|---|---|---|---|
| Tip Adhesion (g) (non aged) | 185.93 (23.37) | 254.64 (25.20) | 234.10 (23.40) |
| Tip Adhesion (g) (aged 60° C. 18 h) | 132.19 (45.89) | 209.99 (104.26) | 428.70 (183.29) |

NOTE:
() = standard deviation. Sample size = 10.

EXAMPLE NO. 10

The following table identifies the effects of using different amounts of a silicone surfactant and an amino-modified silicone surfactant as the lubricant in a catheter tipping operation.

| | 1 | 2 | 3 | 4 |
|---|---|---|---|---|
| Silicone surfactant (%) | 3.00 | 3.00 | 4.50 | 3.00 |
| Amino-modified silicone surfactant (%) | 0.00 | 0.25 | 0.00 | 0.50 |

-continued

| | 1 | 2 | 3 | 4 |
|---|---|---|---|---|
| Vitamin E (%) | 0.125 | 0.00 | 0.25 | 0.125 |
| Cosmocil (PPM) | 50 | 50 | 50 | 50 |
| Water (%) | 96.88 | 96.75 | 95.25 | 96.38 |
| No. of Tips Sticking (out of 60) | 8 | 0 | 1 | 0 |
| Catheter Length (inches) (Target length is 2.0 inches) | 1.99866 | 2.00030 | 1.99953 | 1.99993 |

If the catheter tip sticks, the catheter length will not be 2.0 inches due to stretching of the catheter tip as it is removed from the mandrel. As can be seen, when the lubricant provided adequate lubricity, no tips stuck to the mandrel and the catheter length was very close to the target length of 2 inches.

If the adhesion between the catheter tip and the introducer needle is too high, the needle cannot be easily withdrawn from the catheter after the assembly is placed into the patient's vein. Many thermoplastic materials such as polyurethanes are very sticky in nature and will bond to the surface of a metal under compression. Since the catheter tip sits over the stainless steel needle with an interference fit, it will stick to the needle unless the needle is lubricated.

EXAMPLE NO. 11

The following lubricants were used during the tipping process as a tipping lubricant and to lubricate the needle and the catheter. The control group is included for comparison.

|  | Tipping Lube | Needle Lube | Catheter Lube |
|---|---|---|---|
| Silicone surfactant (%) | 2.375 ± 0.25 | 2.375 ± 0.25 | 4.75 ± 0.25 |
| Amino-modified silicone surfactant (%) | 0.525 ± 0.025 | 0.525 ± 0.025 | 0.525 ± 0.025 |
| Vitamin E (%) | 0.2625 ± 0.0125 | 0.2625 ± 0.0125 | 0.2625 ± 0.0125 |
| Cosmocil (PPM) | 50 | 50 | 50 |
| Water (%) | 96.8375 ± 0.2875 | 98.8375 ± 0.2875 | 94.4625 ± 0.2875 |
|  | Control |  |  |
| DC 12600 cstk Silicone (%) | — | — | 2.0 |
| Masil 1 MM cstk Silicone (%) | — | 2.4 | — |
| PS-513 Amino-modified Silicone (%) | 0.5 | — | — |
| HCFC-141b, Genesolve 2000 (%) | 99.5 | 97.6 | 98.0 |

20 gauge catheter products were assembled by first using the catheter tipping lubricant for tipping the catheter, lubricating the needle and catheter separately using the respective lubricants and finally assembling the catheter assembly. The products were aged at 90° C. for two weeks and tested for tip adhesion. The products were also penetration tested through latex membrane 13.5 mils thick. The results are described below:

|  | Control | | Test | |
|---|---|---|---|---|
| Aging | Tip Adhesion (lbs) | Catheter Drag (g) | Tip Adhesion (lbs) | Catheter Drag (g) |
| 0 Week | 0.19 | 3.0 | 0.12 | 4.8 |
| 1 Week, 90° C. | 0.10 | 4.0 | 0.11 | 3.6 |
| 2 Week, 90° C. | 0.16 | 3.9 | 0.12 | 4.7 |

From the above data, it is clear that the lubricant of this invention stabilizes tip adhesion and the catheter lubricant lubricates the catheter adequately. Furthermore, the properties of the lubricant of this invention are comparable to the control products.

EXAMPLE NO. 12

Other silicone surfactant combinations have been tried. For example, a polyalkylene oxide-modified polydimethylsiloxane block copolymer known as Silwet L7230 which is similar to Silwet L7001 was used in combination with an amino-modified silicone-polyether copolymer known as Silwet Y12593.

| Ingredients | Waterborne Lubricant | Silicone 1 MM cstk |
|---|---|---|
| Silwet L7230 (%) | 4.50 | — |
| Silwet Y12593 (%) | 0.50 | — |
| Vitamin E (%) | 0.25 | — |
| Water (%) | 94.75 | — |
| Silicone 1 MM cstk (%) | — | 2.4 |
| Freon TF (%) | — | 97.6 |

The catheter tubing is swaged into the catheter adapter by using stainless steel wedges. When the catheter assembly is put over the needle assembly it is possible that the stainless steel wedge and the stainless steel needle may rub. Thus there could exist a high resistive force between the two metal surfaces. This becomes even more prominent when the catheter is pushed off of the needle depending upon the angle between the catheter tubing and the needle. A test was devised in which the catheter was held stationary at certain angle rotations to make sure that the needle is rubbing the wedge. The needle was pulled out and the resistive force was measured. The results are given below:

| Product Tested | Resistive Force (lbs) |
|---|---|
| Unlubricated 20(ga) catheter | 0.400 |
| 20(ga) Catheter Lubricated with Silicone | 0.160 |
| 20(ga) Catheter Lubricated with Lubricant of this invention as described above | 0.078 |

The data clearly shows the lubricant effectiveness of the water soluble lubrication system of this invention.

EXAMPLE NO.13

A quaternary ammonium salt was used as a solution stabilizer for the tipping lubricant solution to ensure that the solution is homogenous. A lubricant containing 3% Silwet L7001, 0.5% Sylguard, which is a reactive quaternary compound, 0.25% Urea, and 96.25% water was used for tipping catheters. In all products tested, the tip quality was acceptable. Other quaternary ammonium salts such as benzethonium chloride could also be used.

EXAMPLE NO.14

Different amounts of an amino-modified silicone-polyether were used to establish an acceptable range for use as a tipping lubricant.

|  | 1 | 2 |
|---|---|---|
| Amino-modified silicone surfactant (g) | 1.0 | 10.0 |
| Water (g) | 99.0 | 90.0 |
| Tip Quality | Good | Good |

EXAMPLE NO.15

The two part lubrication solution of this invention was compared to a three part lubrication solution. The following experiment compared a 4% silicone surfactant solution, and a 4% amino-modified silicone surfactant with a three part lubrication solution. This three part lubrication solution used aminopropyl terminated polydimethyl siloxane with a viscosity of 2000 centistokes as the lubricant. Such a product is available from Petrarch Systems under the PS513 trade name. 3% of the PS513 product was mixed with 1% surfactant and 96% water. The surfactant used was Tergitol S and is available from Union Carbide. The tipping results are provided below:

| Parameters | PS513 Emulsion | Silicone Surfactant | Amino-modified Silicone Surfactant |
|---|---|---|---|
| Tip sticking (out of 60) | 0 | 0 | 0 |
| Tipped catheter length (in.) | 2.0019(0.0010)* | 2.0024(0.0014)** | 1.9889(0.0008)* |
| Target length | 2.0000 | 2.0000 | 2.0000 |

Note:
()= standard deviation
*= sample size 10
**= sample size 8

The lubrication results are provided below:

| | Tip Adhesion (lbs) | Catheter Drag (g) |
|---|---|---|
| PS513 Emulsion | 0.21 (0.02) | 3.8 (0.4) |
| Silicone Surfactant | 0.48 (0.05) | 5.8 (1.0) |
| Amino-modified Silicone Surfactant | 0.23 (0.06) | 3.5 (0.3) |

Note:
sample size = 10
() = standard deviation

EXAMPLE NO. 16

Two lubricant solutions for use in the tipping process, lubricating the needles, and lubricating the catheters were tested simultaneously. Two thousand catheter and introducer needle assemblies were produced using one lubricant solution containing Masil 1066C, and another two thousand catheters were produced using another lubricant solution containing Masil 29. The machines ran smoothly. No significant problems surfaced, and the products produced were comparable to the control products similarly produced using the control silicone fluid solutions. These products had good quality tips. They were packaged and sterilized by ethylene oxide and aged at 90° C. for two weeks to compare their performance.

Tipping Lubricant Composition

| Ingredients | Composition No. 1 Percent W/W | Composition No. 2 Percent W/W |
|---|---|---|
| Masil 1066C | 3.50 | — |
| Masil 29 | — | 3.50 |
| Lecithin | 1.00 | 1.00 |
| Cosmocil | 50 ppm | 50 ppm |
| Water | 95.5 | 95.5 |

Needle Lubricant Compositions

| Ingredients | Composition No. 1 Percent W/W | Composition No. 2 Percent W/W |
|---|---|---|
| Masil 1066C | 3.50 | — |
| Masil 29 | — | 3.50 |
| Vitamin E | 0.25 | 0.25 |
| Cosmocil | 50 ppm | 50 ppm |
| Water | 96.25 | 96.25 |

Catheter Lubricant Compositions

| Ingredients | Composition No. 1 Percent W/W | Composition No. 2 Percent W/W |
|---|---|---|
| Masil 1066C | 5.5 | — |
| Masil 29 | — | 5.5 |
| Vitamin E | 0.25 | 0.25 |
| Cosmocil | 50 ppm | 50 ppm |
| Water | 94.25 | 94.25 |

Lubricant Composition for Control Products, Percent (W/W)

| Ingredients | Catheter Tipping Lubricant | Needle Lubricant | Catheter Lubricant |
|---|---|---|---|
| DC360 Silicone 12.50 CSTK | — | — | 2.5 |
| IMM CSTK Silicone | — | 3.0 | — |
| Amino Modified Polydimethylsiloxane PS-513 | 0.65 | — | — |
| Hydrochlorofluorocarbon (HCFC) | 99.35 | 97.0 | 97.25 |

Products produced using Composition No. 1 are identified as Group No. 1 Products. Similarly, those products produced using Composition No. 2 were identified as Group No. 2 Products. The performance of these products are described in Table No. 1 and Table No. 2 below.

TABLE 1

Performance of EtO Sterilized, Non-Aged Products

| Parameters | Group No. 1 | Group No. 2 | Control |
|---|---|---|---|
| Catheter Tip Adhesion (lbs) | 0.29 (0.03) | 0.21 (0.06) | 0.39 (0.11) |
| Latex Penetration | | | |
| Needle tip (g) | 16.9 (1.9) | 16.6 (1.1) | 15.2 (1.7) |
| Catheter tip (g) | 16.7 (2.0) | 17.6 (2.6) | 11.8 (0.8) |
| Catheter drag (g) | 4.2 (0.5) | 5.2 (0.9) | 3.7 (0.7) |
| Needle/Adapter Pull (lbs) | 46.9 (3.8) | 50.1 (5.0) | 50.0 (4.3) |
| Catheter/Adapter Pull (lbs) | 2.28 (0.21) | 2.45 (0.24) | 2.35 (0.19) |

TABLE 2

Performance of EtO Sterilized, 2 Weeks Aged at 90° C. Products

| Parameters | Group No. 1 | Group No. 2 | Control |
|---|---|---|---|
| Catheter Tip Adhesion (lbs) | 0.89 (0.29) | 0.26 (0.09) | 1.05 (0.11) |
| Latex Penetration | | | |
| Needle tip (g) | 21.4 (2.6) | 18.1 (1.9) | 13.6 (1.4) |
| Catheter tip (g) | 17.4 (4.8) | 18.8 (3.4) | 12.1 (1.0) |
| Catheter drag (g) | 3.2 (0.6) | 3.7 (0.9) | 3.0 (0.3) |

TABLE 2-continued

Performance of EtO Sterilized, 2 Weeks Aged at 90° C. Products

| Parameters | Group No. 1 | Group No. 2 | Control |
|---|---|---|---|
| Needle/Adapter Pull (lbs) | 45.1 (3.0) | 47.9 (4.3) | 41.9 (4.4) |
| Catheter/Adapter Pull (lbs) | 2.43 (0.14) | 2.41 (0.12) | 2.47 (0.18) |

Performance test results before and after aging the products at 90° C. for two weeks indicate that the performance of Group No. 1 and Group No. 2 products are comparable to the control.

Thus, it is seen that a new lubrication system is provided that is inexpensive, easy to control, safe, non-toxic and "environmentally friendly."

We claim:

1. A lubrication solution for a medical device, comprising: a silicone based water soluble lubricant; and water.

2. The lubrication solution of claim 1, wherein the silicone based water soluble lubricant is a silicone surfactant lubricant.

3. The lubrication solution of claim 2 wherein the silicone surfactant lubricant is a block copolymer polyalkylene oxide-modified polydimethylsiloxane.

4. The lubrication solution of claim 2 wherein the silicone surfactant lubricant is an amino-modified silicone polyether copolymer.

5. The lubrication solution of claim 3 wherein the silicone surfactant lubricant also includes an amino-modified silicone polyether copolymer.

6. The lubrication solution of claim 1 wherein the silicone based water soluble lubricant is an alkylene oxide modified silicone glycol.

7. A medical device having a surface with a silicone based water soluble lubricant deposited thereon.

8. The medical device of claim 7 wherein the silicone based water soluble lubricant is a silicone surfactant.

9. The medical device of claim 8 wherein the silicone surfactant is a block copolymer polyalkylene oxide-modified polydimethylsiloxane.

10. The medical device of claim 9 wherein the silicone surfactant also includes an amino-modified silicone-polyether copolymer.

11. The medical device of claim 8 wherein the silicone surfactant is an amino-modified silicone-polyether copolymer.

12. The medical device of claim 7 wherein the silicone based water soluble lubricant is an alkylene oxide-modified silicone glycol.

13. A method for forming a shaped tip on a catheter comprising:

applying a silicone based water soluble lubricant to a tip of an untipped catheter tubing;

placing the untipped catheter tubing on a mandrel;

heating the untipped catheter tubing to soften the tip of the tubing;

engaging the mandrel with a die to form the catheter tip; and removing the shaped catheter tubing from the die and mandrel.

14. The method of claim 13 wherein the silicone based water soluble lubricant is applied to a tip of an untipped catheter tubing by applying a lubricant solution of the silicone based water soluble lubricant and water to the tip.

15. The method of claim 14 wherein the silicone based water soluble lubricant is a silicone surfactant.

16. The method of claim 14 wherein the silicone based water soluble lubricant is an alkylene oxide modified silicone glycol.

* * * * *